(12) United States Patent
Carron et al.

(10) Patent No.: US 8,668,494 B2
(45) Date of Patent: Mar. 11, 2014

(54) ADJUSTABLE ANGLE PROPHY ANGLE ADAPTER

(75) Inventors: Chris J. Carron, Bloomsdale, MO (US); David G. Grither, Ste. Genevieve, MO (US)

(73) Assignee: Angstrom Manufacturing, Inc., Bloomsdale, MO (US)

(*) Notice: Subject to any disclaimer, the term of this patent is extended or adjusted under 35 U.S.C. 154(b) by 28 days.

(21) Appl. No.: 13/371,026

(22) Filed: Feb. 10, 2012

(65) Prior Publication Data

US 2012/0214126 A1  Aug. 23, 2012

Related U.S. Application Data

(60) Division of application No. 12/503,151, filed on Jul. 15, 2009, now abandoned, which is a continuation-in-part of application No. 11/862,628, filed on Sep. 27, 2007, now Pat. No. 8,123,523, which is a continuation-in-part of application No. 11/682,927, filed on Mar. 7, 2007, now abandoned, which is a continuation-in-part of application No. 11/189,193, filed on Jul. 26, 2005, now Pat. No. 7,422,433.

(51) Int. Cl.
*A61C 1/12* (2006.01)
*A61C 1/18* (2006.01)
*A61C 17/22* (2006.01)

(52) U.S. Cl.
USPC ............ 433/130; 433/109; 433/124; 433/133

(58) Field of Classification Search
USPC ........................ 433/103–133; 285/272–282; 384/507–509, 96; 403/58, 99, 101, 403/102, 103; 606/170, 180, 190

See application file for complete search history.

(56) References Cited

U.S. PATENT DOCUMENTS

| | | | | | |
|---|---|---|---|---|---|
| 991,501 | A | * | 5/1911 | Graves | 285/147.1 |
| 1,170,524 | A | * | 2/1916 | Fernald | 433/130 |
| 1,194,679 | A | * | 8/1916 | Strom | 384/507 |
| 1,379,880 | A | * | 5/1921 | Seaborn | 433/130 |
| 2,548,450 | A | * | 4/1951 | Staunt | 433/124 |
| 3,101,542 | A | * | 8/1963 | Fodor | 433/105 |
| 3,509,629 | A | * | 5/1970 | Fukuda et al. | 433/114 |
| 4,278,429 | A | * | 7/1981 | Straihammer et al. | 433/126 |
| 4,690,012 | A | * | 9/1987 | Dahlquist et al. | 74/490.06 |
| 5,352,234 | A | * | 10/1994 | Scott | 606/170 |
| 5,372,420 | A | * | 12/1994 | Van Deursen et al. | 366/129 |
| 5,549,634 | A | * | 8/1996 | Scott et al. | 606/170 |

(Continued)

*Primary Examiner* — Todd Manahan
*Assistant Examiner* — Michael R Ballinger
(74) *Attorney, Agent, or Firm* — Steven M. Greenberg, Esq.; Kara A. Brotman, Esq.; CRGO Law

(57) ABSTRACT

An adjustable angle adapter for a prophy angle comprises a nose, a rotating member, a body, a shaft, a pivot, and a multi-axis rotation joint. The nose is configured to receive a portion of a prophy angle. The rotating member is positioned within the nose. The body is adjustably connected to the nose. The shaft is positioned within the body. The pivot connects the body to the nose and includes a groove configured for a ball bearing that is passed through a channel formed within the pivot and the body. Also, the channel is parallel to the rotational axis of the shaft. The multi-axis rotation joint connects the shaft to the rotating member. The nose is rotatable relative to the body into a first configuration and a second configuration.

18 Claims, 14 Drawing Sheets

(56) References Cited

U.S. PATENT DOCUMENTS

| | | | | |
|---|---|---|---|---|
| 5,575,799 | A | * | 11/1996 | Bolanos et al. ............... 606/139 |
| 5,699,810 | A | * | 12/1997 | Pallikaris ...................... 128/898 |
| 5,950,268 | A | * | 9/1999 | Murphy et al. ................... 15/28 |
| 6,019,518 | A | * | 2/2000 | Yoon ............................. 384/560 |
| 6,050,989 | A | * | 4/2000 | Fox et al. ......................... 606/1 |
| 6,837,624 | B2 | * | 1/2005 | Buard et al. .................. 384/531 |
| 7,328,635 | B2 | * | 2/2008 | Hu ............................... 81/177.9 |
| 2004/0164670 | A1 | * | 8/2004 | Nanni et al. .................. 313/503 |

* cited by examiner

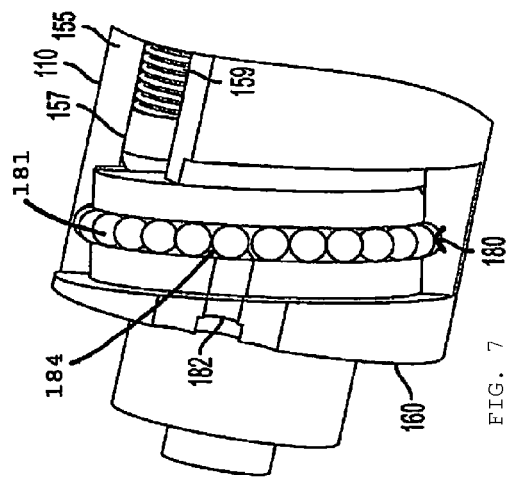
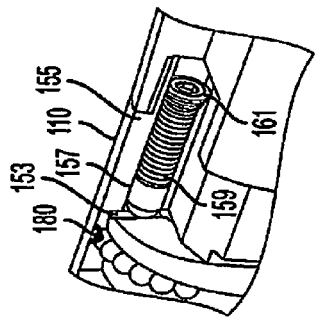
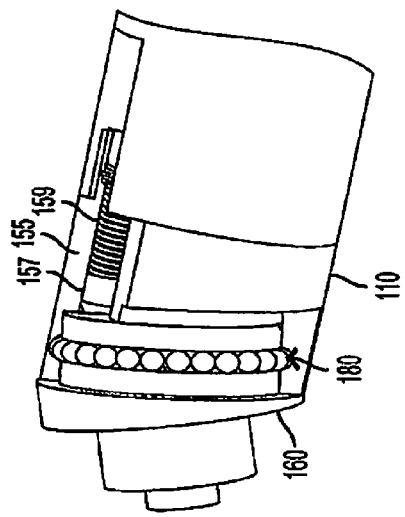
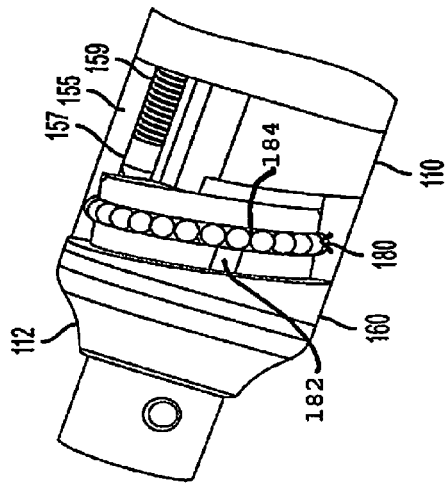

ADJUSTABLE ANGLE PROPHY ANGLE ADAPTER

CROSS-REFERENCE TO RELATED APPLICATIONS

This application is a divisional of U.S. application Ser. No. 12/503,151, filed on Jul. 15, 2009, now abandoned, which is a Continuation-In-Part of U.S. application Ser. No. 11/862,628 filed on Sep. 27, 2007, now U.S. Pat. No. 8,123,523, a Continuation-In-Part of U.S. application Ser. No. 11/682,927 filed on Mar. 7, 2007, now abandoned, and a Continuation-In-Part of U.S. application Ser. No. 11/189,193, filed on Jul. 26, 2005, now U.S. Pat. No. 7,422,433, all of which are incorporated herein by reference in their entirety.

BACKGROUND OF THE INVENTION

1. Field of the Invention

The disclosure relates generally to dental instruments and, more specifically, to adapters for use with prophy angles.

2. Description of the Related Art

Dental prophylaxis angles, generally referred to as "prophy angles," are commonly used dental instruments for providing rotation for dental tools such as brushes, prophy cups, or other receptacles used in cleaning/polishing teeth. Referring to FIGS. 17 and 18, a prophy angle 10 typically includes a housing 16 having a neck 18 and a head portion 14 extending at approximately a 90° angle to the neck 18, which increases the ability of a dentist to reach various surfaces of the teeth of a patient. A drive shaft or rotating member 12 can be located within the housing 16 and attached to a driven gear 20 in the head of the prophy angle. Prophy angles 10 are generally affixed to an adapter or hand piece (not shown), which connects the prophy angle to a drive source (not shown), thereby enabling a rotating motion of the rotating member 12 and driven gear 20 of the prophy angle and any affixed dental tool.

Prophy angles 10 are commonly manufactured from lightweight plastic to make them disposable, thereby increasing overall sterility in the dental environment. An issue associated with making the prophy angles 10, and their constituent elements, such as the rotating member 12, from plastic is the ability of the hand piece to engage the rotating member 12 without slipping and to engage the rotating member 12 without excessive damage to the rotating member 12. Another issue associated with the use of prophy angles 10 is the widespread use of many different and incompatible types of couplings between the drive source and the hand piece and between the hand piece and the prophy angle 10. Yet another issue associated with the use of prophy angles 10 is the number of adapters needed to provide different orientations.

BRIEF SUMMARY OF THE INVENTION

Embodiments of the invention address deficiencies of the art with respect to adjustable angle adapters for prophy angles. An adjustable angle adapter for a prophy angle can comprise a nose, a rotating member, a body, a shaft, a pivot, and a multi-axis rotation joint. The nose is configured to receive a portion of a prophy angle. The rotating member is positioned within the nose. The body is adjustably connected to the nose. The shaft is positioned within the body. The pivot connects the body to the nose and can include a groove configured for a ball bearing and opposing and mating faces which define a plane that is at an angle, other than perpendicular, to a rotational axis of the rotating member and a rotational axis of the shaft. Further, the ball bearing can be passed through a channel formed within the pivot and the body, where the channel is parallel to the rotational axis of the shaft. The multi-axis rotation joint connects the shaft to the rotating member. The nose is rotatable relative to the body into a first configuration and a second configuration. In addition, the nose can rotate relative to the body about a point on the plane, where the point is at the intersection of the plane and the rotational axis of the rotating member and at the intersection of the plane and the rotational axis of the shaft.

In the first configuration, the shaft and the rotating member share a common rotational axis, and in the second configuration, a rotational axis of the shaft is at a non-zero degree angle to a rotational axis of the rotating member. A lock is included. In an unlocked configuration of the lock, the nose is rotatable relative to the body, and in a locked configuration of the lock, the lock preventing the nose from rotating relative to the body. A pivot connects the body to the nose.

In certain aspects, the nose rotates relative to the body about an axis substantially perpendicular to a rotational axis of the shaft and/or a rotational axis of the rotating member. In other aspects, the pivot comprises opposing and mating faces that are at an angle, other than perpendicular, to a rotational axis of the rotating member and a rotational axis of the shaft. The nose is rotatable relative to the body into at least a first configuration and a second configuration while the shaft is rotating. The nose rotates relative to the body about an axis that intersects an intersection point between a rotational axis of the rotating member and a rotational axis of the shaft.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein:

FIG. 6 is a partial cross-sectional view of the pivot, coupler, and lock;

FIG. 7 is another partial cross-sectional view of the pivot, coupler, and lock;

FIG. 8 is yet another partial cross-sectional view of the pivot, coupler, and lock;

FIG. 9 is still another partial cross-sectional view of the pivot, coupler, and lock;

DETAILED DESCRIPTION OF THE INVENTION

Figure 1A:
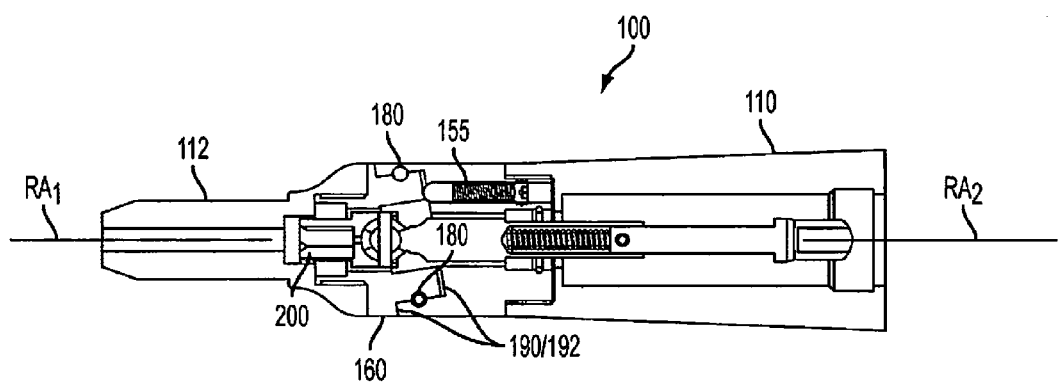
FIGS. 1A and 1B are side cross-sectional views of a second adjustable angle adapter, respectively in a straight configuration and a contra configuration, in accordance with the inventive arrangements.
Figure 1B:
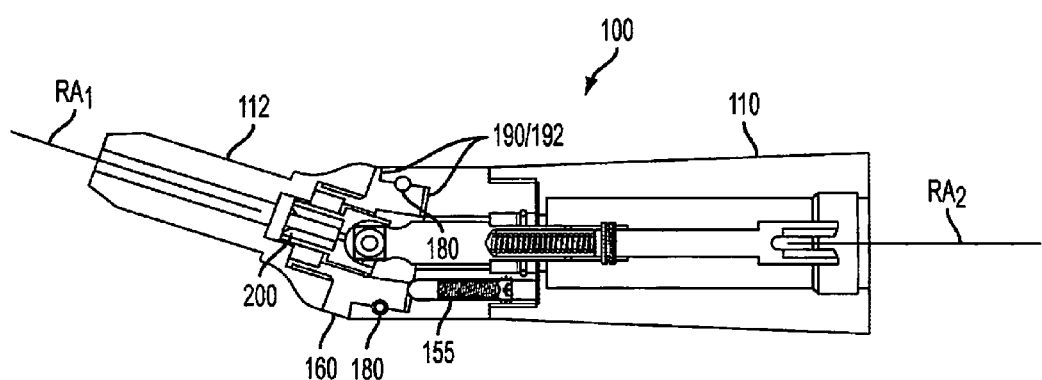
Figure 2:
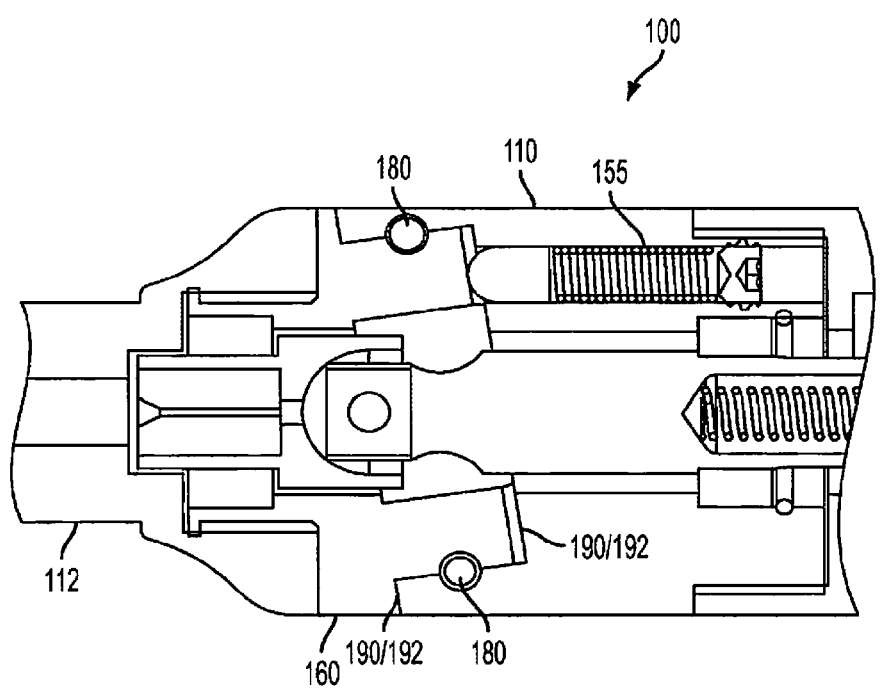
FIG. 2 is an enlarged side cross-sectional view of the second adjustable adapter of FIG. 1A.
Figure 3:
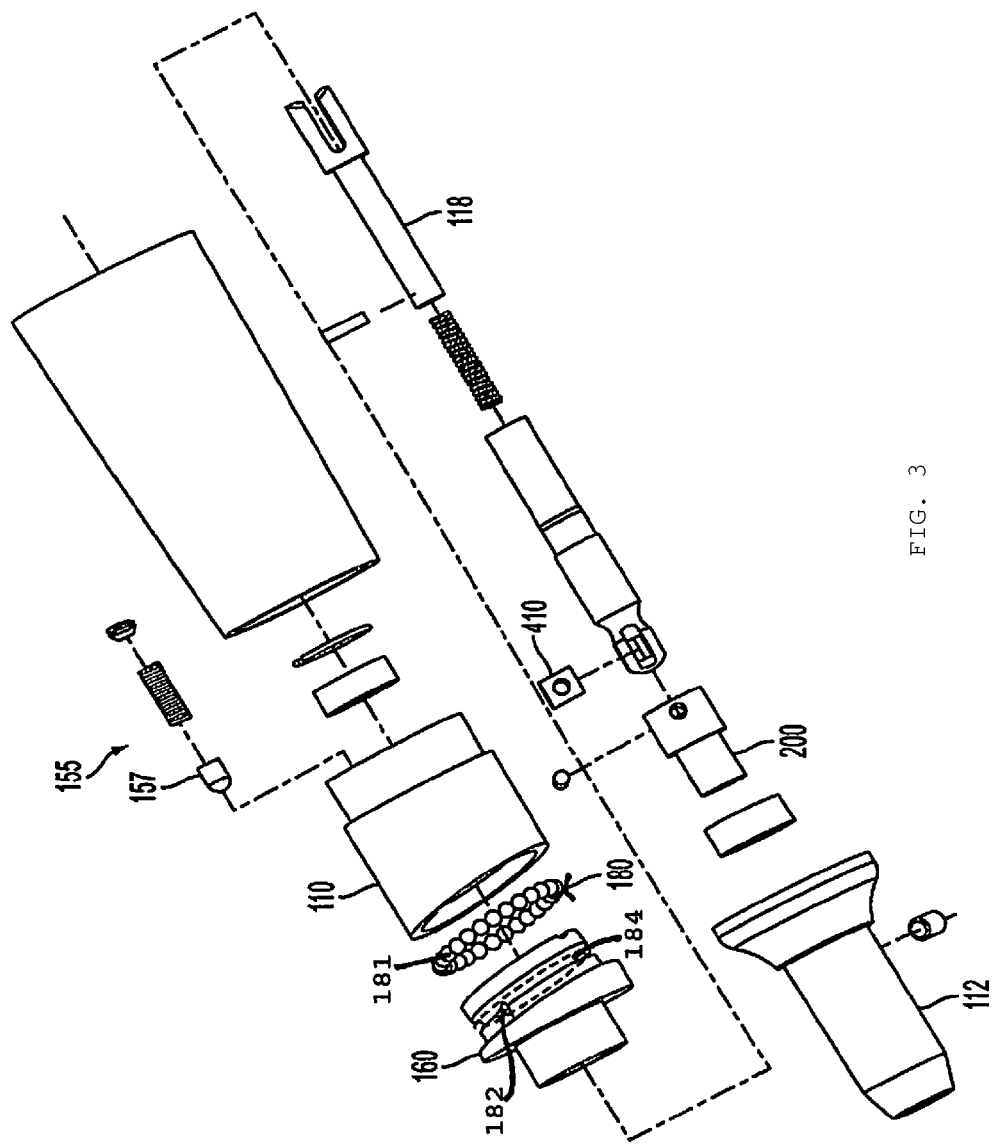
FIG. 3 is an exploded, perspective view of the adjustable angle adapter of FIGS. 1A and 1B.
Figure 4A:
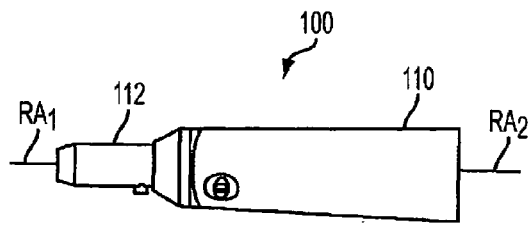
FIGS. 4A and 4B are, respectively, top and side views of the adjustable angle adapter in a straight configuration.
Figure 4B:
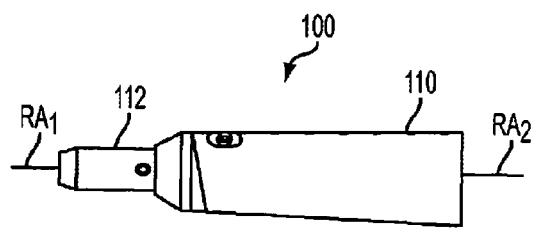

Referring to FIGS. 1A-9, a mechanism by which the nose 112 is rotated relative to the body 110 is illustrated. The mechanism includes a pivot 160, which is connected to both the nose 112 and the body 110. The pivot 160 is rotationally stationary relative to one of the nose 112 and body 110, and is rotationally connected to the other of the nose 112 and body 110. As illustrated, the pivot 160 is fixed relative to the nose 112 and rotationally connected to the body 110. Many devices are known as being capable of rotationally connecting one feature to another feature, and the first mechanism is not limited in the manner by which the pivot 160 is rotationally connected to the body 110. For example, the pivot 160 is connected to the body 110 using a coupler 180, such as a ring or bearings 181, between the pivot 160 and the body 110.

Both the pivot 160 and the body 110 respectively include opposing and mating faces 190, 192 that are at an angle, other than perpendicular, to the rotational axis $RA_1$ of the collet 200 and the rotational axis $RA_2$ of the shaft 118. In one aspect, these angles of the mating faces 190, 192 relative to the rotational axes $RA_1$, $RA_2$ are the same. Depending upon the orientation of the body 110 relative to the nose 112, these angles either (i) cancel each other out (i.e., FIG. 1A) such that a shared rotational axis exists between the body 110 and the nose 112, (ii) combine such that the angle between the rotational axis $RA_1$ of the collet 200 and the rotational axis $RA_2$ of the shaft 118 is twice the angle between one of the mating faces 190, 192 and one of the rational axes $RA_1$, $RA_2$, or (iii) the angle between the rotational axis $RA_1$ of the collet 200 and the rotational axis $RA_2$ of the shaft 118 is somewhere between 0° and twice the angle between one of the mating faces 190, 192 and one of the rational axes $RA_1$, $RA_2$).

In current aspects of the adjustable angle adapter 100, the angle between the rotational axis $RA_2$ of the shaft 118 and the rotational axis $RA_1$ of the collet 200 is adjustable between 0° and 18°±10°. In certain current aspects, the angle is adjustable between 0° and 18°. To provide an adjustment to an 18° angle, the angle between each of the mating faces 190, 192 and the respective rational axes $RA_1$, $RA_2$ would be 9°.

The adjustable angle adapter 100 also includes a lock 155 that prevents the nose 112 from rotating relative to the body 110. Many devices are known as being capable of preventing one feature from rotating relative to another feature, and the adjustable angle adapter 100 is not limited in the manner to a particular type of lock 155 so capable. However, in certain aspects of the adjustable angle adapter 100, the lock 155 includes a movable pin 157 that extends between the body 110 and the nose 112. In a withdrawn, unlocked position, the pin 157 is withdrawn into either one of the body 110 and nose 112. However, in an extended, locked position, the pin 157 intersects both of the mating faces 190, 192 of the body 110 and nose 112, which prevents rotation of the nose 112 relative to the body 110.

Figure 5A:
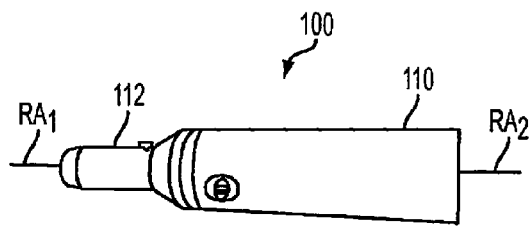
FIGS. 5A and 5B are, respectively, top and side views of the adjustable angle adapter in a contra configuration.
Figure 5B:
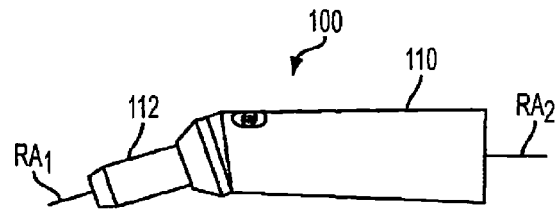

FIGS. 4A-4B and 5A-5B illustrate the steps involved in adjusting the adjustable angle adapter 100 from the first configuration (i.e., a 0° angle or shared rotational axis RA) to the second configuration (i.e., an 18° angle between the rotational axes $RA_1$, $RA_2$. Staring with FIGS. 4A-4B, the body 110 is twisted, relative to the body 110, about the rotational axis $RA_1$ of the collet 200. This twisting motion causes the rotational axis $RA_1$ of the collet 200 to diverge from the rotational axis $RA_2$ of the shaft 118, as shown in FIG. 5B.

FIGS. 6-9 illustrate further aspects of the pivot 160, coupler 180, and lock 155. Referring specifically to FIG. 7, in certain aspects, a channel 182 can be formed within the pivot 160 and the body 110 through which the bearings 181 of the coupler 180 can be introduced into a groove 184 between the body 110 and the pivot 160, which respectively act as races of a ball bearing 181. This channel 182 can be subsequently plugged and/or stopped by rotating the pivot 160 relative to the body 110. In this manner, the balls 181 are prevented from exiting the groove. In addition, this channel 182 can be covered by the nose 112, when the nose 112 and the body 110 are coupled, as illustrated in FIGS. 4A through 5B.

Although not limited to this specific configuration, the lock 155 can include a pin 157, a biasing member 159, and an adjustable stop 161. The pivot 160 can also include a receiving portion 153 (e.g., a slot or dimple) that receives the pin 157. Upon the body 110 rotated relative to the pivot 160 along a particular orientation, the receiving portion 153 is in-line with the pin 157, and the biasing member 159 biases the pin 157 into the receiving portion 153. Thus, for a user to rotate the body 110 relative to the pivot 160 (and also the nose 112), a sufficient force needs to be exerted to bias the pin 157 out of the receiving portion 153.

In certain aspects, the lock 155 includes an adjustable stop 161. The adjustable stop 161 can serve different functions. For example, by moving the stop 161 towards the pin 157, the biasing member 157 is further compressed, making it harder to rotate the body 110 relative to the pivot 160 when the pin 157 has engaged the receiving portion 153. Conversely, by moving the stop 161 away from the pin 157, it becomes easier to rotate the body 110 relative to the pivot 160 when the pin 157 has engaged the receiving portion 153. Additionally, the stop 161 can be moved towards the pin 157 to such a degree that the biasing member 159 is unable to be compressed sufficiently enough to allow the pin 157 to clear the receiving portion 153. In such a circumstance, rotation of the body 110 relative to the pivot 160 is effectively prevented. Thus, an adjustable adapter 110 can be permanently or semi-permanently modified into a non-adjustable adapter.

Figure 10A:
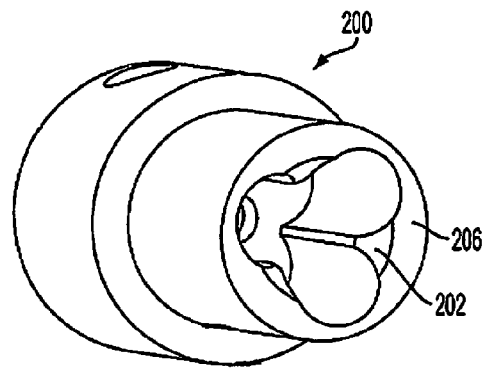
FIGS. 10A-10C are, respectively, a front perspective view, a front plan view, and a side cross-sectional view of a collet in accordance with the inventive arrangements.
Figure 10B:
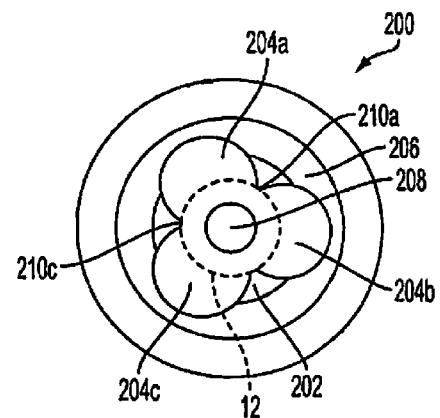
Figure 10C:
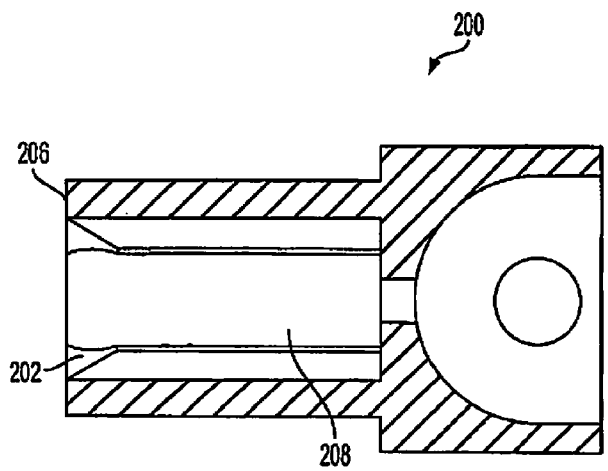

FIGS. 10A-10C further illustrate the collet 200. The collet 200 of the adapter 100 is adapted to receive and hold the rotating member 12 of the prophy angle. In certain aspects of the adapter 100, the collet 200 is not limited in the manner in which the collet 200 receives and holds the rotating member 12, and any configuration of the collet 200 so capable is acceptable for use with the adapter 100.

In certain aspects of the adapter 100, the collet 200 includes a plurality of extensions 210a-210c for receiving the rotating member 12. The innermost portions of the extensions 210a-210c (210b not labeled) define an inner collet bore 208 having a diameter slightly less than the diameter of the rotating member 12. In this manner, upon the rotating member 12 being positioned within the inner collet bore 208, an interference fit or friction grip exists between the plurality of extensions 210a-210c and the rotating member 12. The interference fit allows the extensions 210a-210c to hold onto the rotating member 12 and to transfer rotation from the collet 200 to the rotating member 12. In certain aspects of the collet 200, the innermost portions of the extensions 210a-210c define an inner collet bore 208 having a fixed diameter.

As best shown in FIG. 10A, the outer edge of each extension 210a-210c (not labeled in FIG. 10A) may also include a concave surface. The concave surfaces of the extensions 210a-210c can define the outer circumference of the inner collet bore 208 of the collet 200. These concave surfaces also mate with the outer surface of the rotating member 12 to form the interference fit between the plurality of extensions 210a-210c and the rotating member 12. Although not limited in this manner, the radius of the concave surfaces of the extensions 210a-210c is substantially equal to the radius of the collet bore 208. Although not limited in this manner, in certain aspects of the collet 200, the concave surfaces define less than 20% of the circumference of the collet bore 208.

The collet 200 may also include longitudinal chamfers 202 on the extensions 210a-210c. The chamfers may extend from a collet distal end 206 along each extension 210a-210c and slope inwardly towards the rotational axis of the collet 200. The longitudinal chamfers 202 provide a guide for receiving the rotating member 12. As the rotating member 12 is moved into the collet 200, the longitudinal chamfers 202 guide the rotating member 12 toward the inner collet bore 208. Although not limited in this manner, a face of the longitudinal chamfers 202 may be angled at about 60°±15° relative to the face of the distal end 206 of the collet 200.

The manner in which the inner collet bore 208 is formed is not limited. For example, the inner collet bore 208 may be formed by drilling the collet 200 along its centerline. By forming the inner collet bore 208 is this manner, the concave surfaces at the outer edge of each extension 210a-210c may also be formed. Also, the extensions 210a-210c may be formed by drilling offset bores 204a-204c, which have a centerline offset from the centerline of the collet 200. Although the term "drilling" is used herein, other methodology used to form bores/holes is also acceptable.

Many types of joints are capable of transferring rotation from a first rotating member to a second rotating member, which is positioned off-axis from the first rotating member, and the present adjustable angle adapter 100 is not limited as to a particular type of joint so capable. Examples of these joints are illustrated in FIGS. 11A-11D, 12A, 12B, 13, 14, and 15, However, in a current aspect of the adapter 100, the multi-axis rotation joint is a yoke and joint, as illustrated in FIGS. 11A-11C and 12A-12B.

Figure 11A:
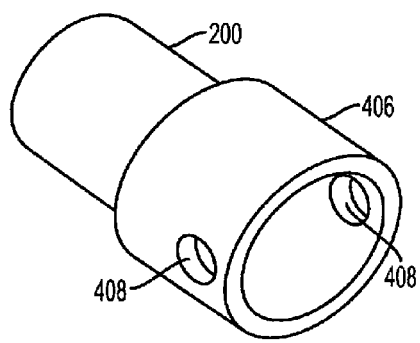
FIGS. 11A-11D are, respectively, a perspective view of a receiver, a perspective view of the receiver and a second pin, a perspective view of a first pin and the second pin, and a perspective view of the first pin and the second pin position within a head of a yoke and pin joint in accordance with the inventive arrangements.

Referring to FIGS. 11A-11C and 12A-12B, elements of a multi-axis rotation joint are illustrated. Referring to FIG. 11A, the collet 200 is connected to a receiver 406 for receiving a head 410 (illustrated in FIGS. 3 and 12A, for example) of the multi-axis rotation joint. Although shown connected to the collet 200, the receiver 406 may be integral with the collet 200. Alternatively, another member (not shown) may be positioned between the receiver 406 and the collet 200. The use of a multi-axis rotation joint advantageously reduces back lash, which is inherent in may types of joints.

Figure 11B:
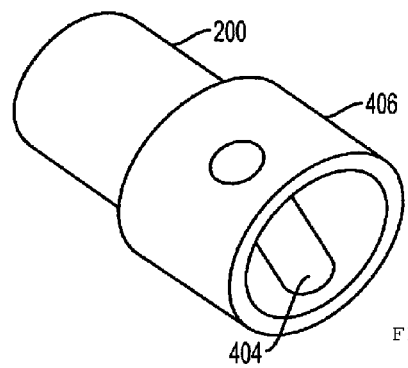

Referring to FIGS. 11A and 11B, the receiver 406 includes openings 408 into which a second pin 404 is positioned. Although the second pin 404 may rotate within the openings 408 of the receiver 406, in a current aspect of the multi-axis rotation joint, the second pin 404 is positionally and rotationally fixed relative to the receiver 406. In so doing, the second pin 404 is prevented from moving within the receiver 406. Since the receiver 406, and thus the ends of the second pin 404, can rotate about the rotational axis $RA_1$ of the collet 200 at very high speeds, any movement of the ends of the second pin 404 beyond the outer circumference of the receiver 406 may cause engagement between the ends of the second pin 404 and inner surfaces of the nose 112 and/or the body 110 of the adapter 100. This engagement may cause failure of or damage to the adapter 100 and/or the multi-axis rotation joint.

The manner in which the second pin 404 is prevented from moving within the receiver 406 is not limited as to a particular technique or arrangement. For example, the second pin 404 can be attached to the receiver, for example, via welding or gluing. However, in a current aspect of the multi-axis rotation joint, the second pin 404 is sized slightly greater than the size of the openings 408 of the receiver 406 such that upon inserting the second pin 404 into openings 408, an interference fit exists between the second pin 404 and the openings 408.

Figure 11C:
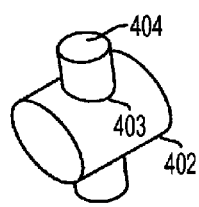
Figure 11D:
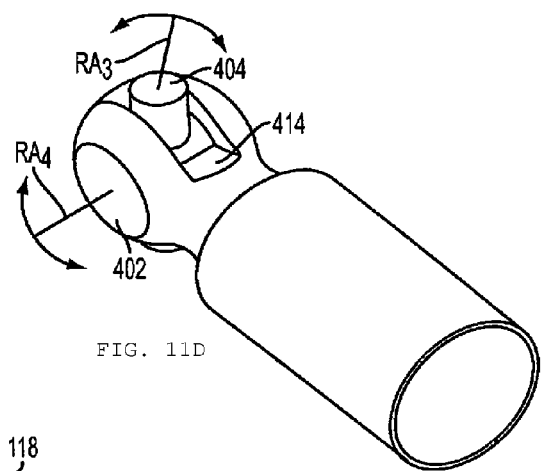
Figure 12A:
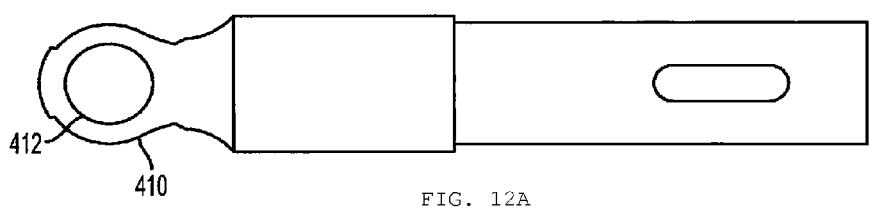
FIGS. 12A and 12B are, respectively, side and top views of the head of the multi-axis rotation joint and a shaft to which the head is connected.
Figure 12B:
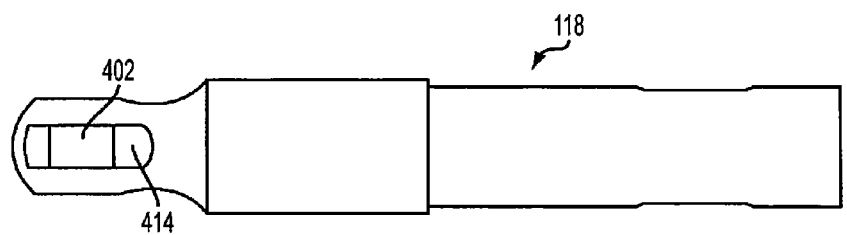

Referring to FIGS. 11C and 11D, the second pin 404 is positioned within an opening 403 of a first pin 402, and the first pin 402 is positioned within a head. As also illustrated in FIGS. 12A and 12B, the head 410 includes slots 414 through which the second pin 404 extends. As presently configured, the first pin 402 rotates within and relative to the head bore 412 of the head 410 about a rotational axis $RA_4$, and the second pin 404 rotates within relative to the first pin 402 about a rotational axis $RA_3$. The outside diameter of the second pin 404 is somewhat less than the inside diameter of the inside diameter of the opening 403 of the first pin 402 to form a close tolerance slip fit between the second pin 404 and the first pin 402. Similar, the outside diameter of the first pin 402 is somewhat less than the inside diameter of the head bore 412 of the head 410 to form a close tolerance slip fit between the first pin 402 and the head bore 412 of the head 410.

Although not limited as to a particular range of rotation or to the particular manner described herein, the first pin 402, while within the head 410, is limited in its range of rotation by the length of the slot 414 in the head 410. As the length of the slot 414 increases, the range of the rotation of the first pin 402 within the head 410 is also increased. Conversely, upon the length of the slot 414 decreasing, the range of rotation of the first pin 402 within the head 410 is also decreased. The width of the slots 414 may be slightly less than the outside diameter of the second pin 404 to allow the second pin 404 to move from side-to-side within the slots 414.

With regard to the range of rotation of the second pin 404 within the first pin 402, the range of rotation is not necessarily limited when the first pin 402 is within the second pin 404 alone. However, upon the joint 400 being full assembled, the range or ration of the second pin 404 within the first pin 402 may be limited to some degree by interference between the collet 200 and the shaft 118.

Although illustrated as the head 410 being connected to the shaft 118 and the receiver 406 being connected to the collet 200, the multi-axis rotation joint is not limited in this manner. For example, the head 410 may be connected to the collet 200, and the receiver 406 may be connected to the shaft 118.

Unlike many other types of joints, a multi-axis rotation joint allows for the angle between the rotational axis $RA_2$ of the shaft 118 and the rotational axis $RA_1$ of the collet 200 to be varied. Thus, use of the multi-axis rotation joint permits the adjustable angle adapter 100 to be adjusted while the shaft 118 and collet 200 are rotating. To further enable the adjustable angle adapter 100 to be adjusted during the rotation of the shaft 118 and collet 200, the nose 112 pivots relative to the body 100 about a point that is congruent with the intersection point between the rotational axes $RA_1$, $RA_2$ of the collet 200 and shaft 118.

Figure 13:
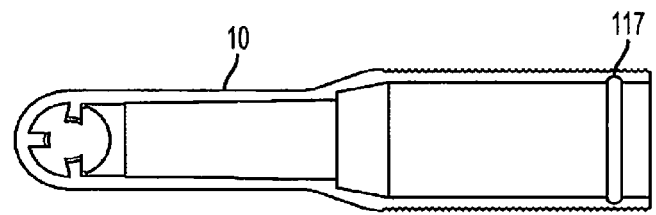
FIG. 13 is a side, cross-sectional view of an improved prophy angle in accordance with the inventive arrangements.
Figure 14:
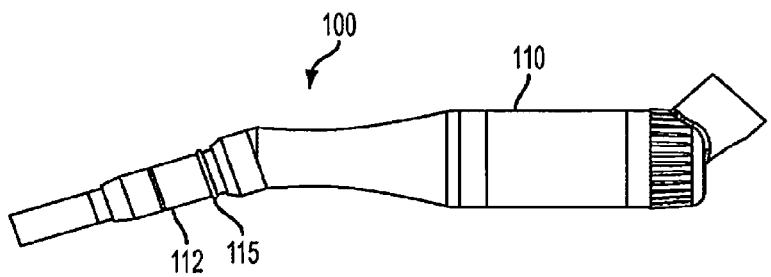
FIG. 14 is a side view of the adjustable angle adapter with a lip in accordance with the inventive arrangements.
Figure 15:
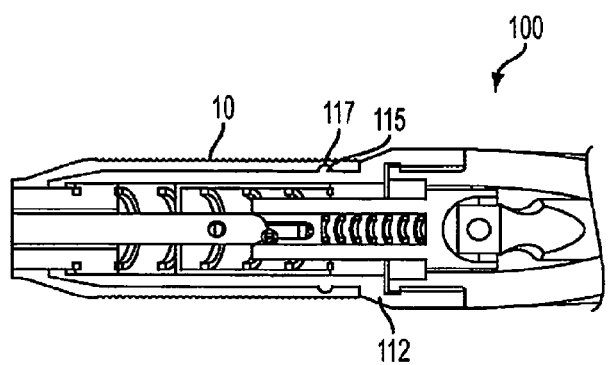
FIG. 15 is a side, cross-sectional view of the improved prophy angle and adjustable angle adapter of FIGS. 13 and 14 in accordance with the inventive arrangements.

Referring to FIGS. 13-15, and improved prophy angle 10 and nose 112 is illustrated for an adjustable angle adapter 100 having a body 110. One of the nose 112 and prophy angle 10 includes a lip 115, and the other of the nose 112 and prophy angle 10 includes a groove 117 for receiving the lip 115. In this manner, the prophy angle 10 may be retained on the nose 112 while still being able to rotate relative to the nose 112.

Figure 16A:
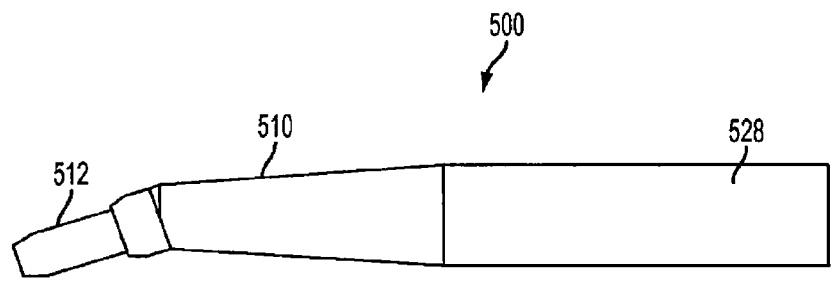
FIGS. 16A and 16B are, respectively, side and side cross-sectional views of an adapter with an integral micromotor.
Figure 16B:
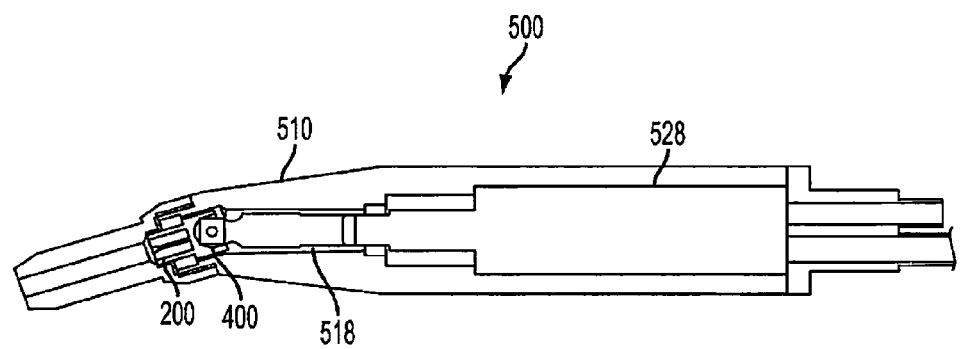
Figure 17:
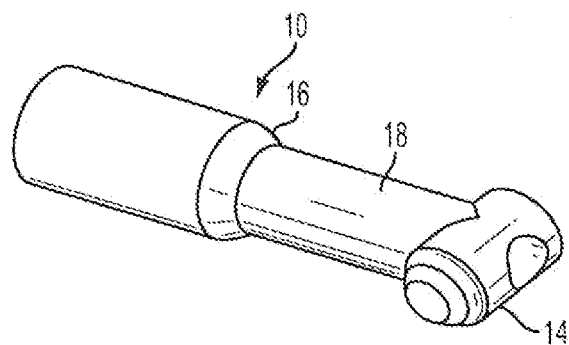
FIG. 17 is a perspective view of a prophy angle according to the prior art.
Figure 18:
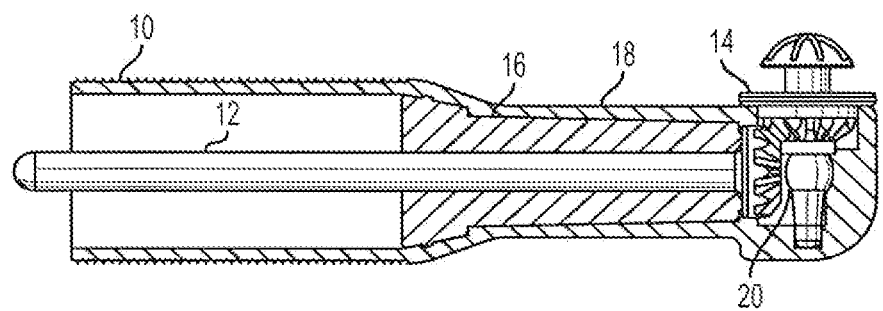
FIG. 18 is a side cross-sectional view of the prophy angle according to the prior art.
Figure 19A:
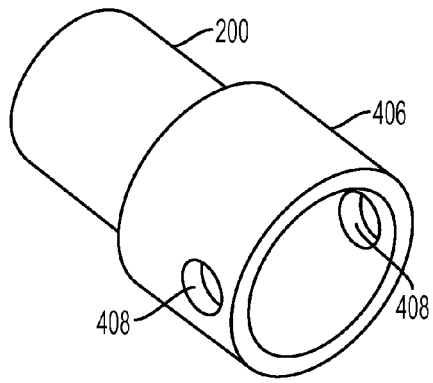
Figure 19B:
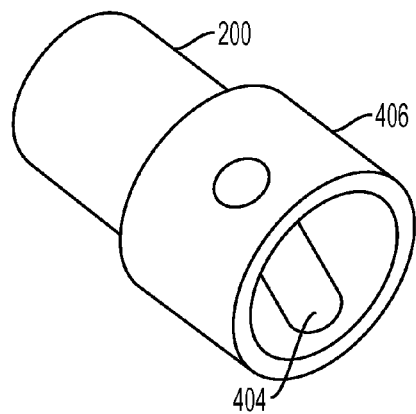
Figure 19C:
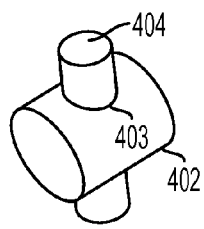
Figure 19D:
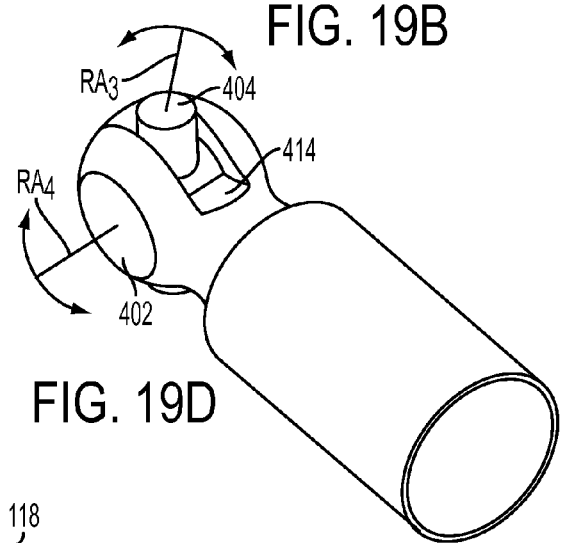
Figure 20A:
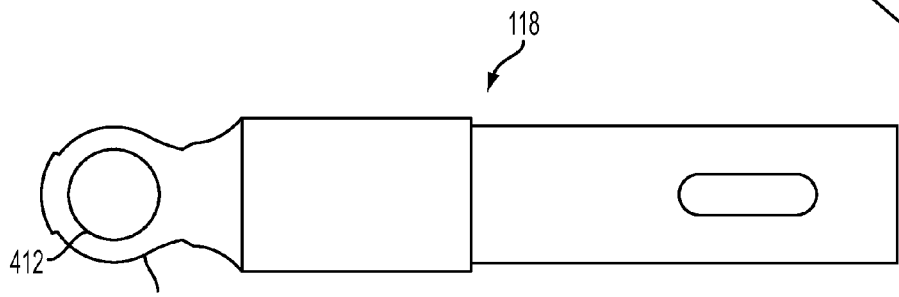
Figure 20B:
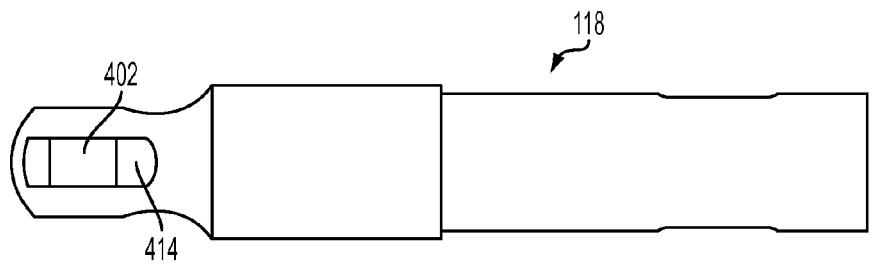
Figure 21:
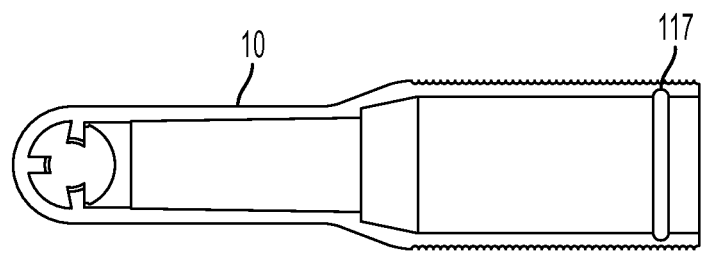
Figure 22:
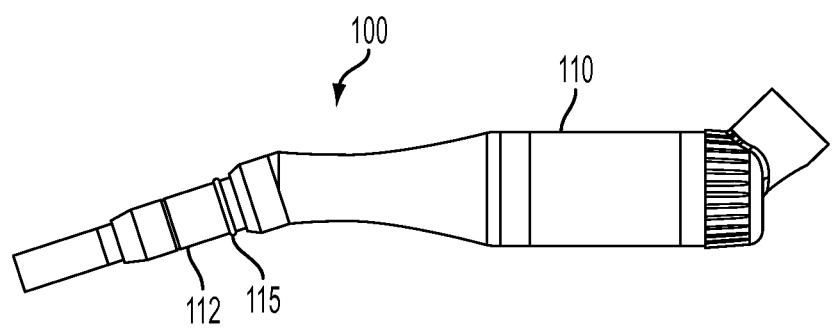
Figure 23:
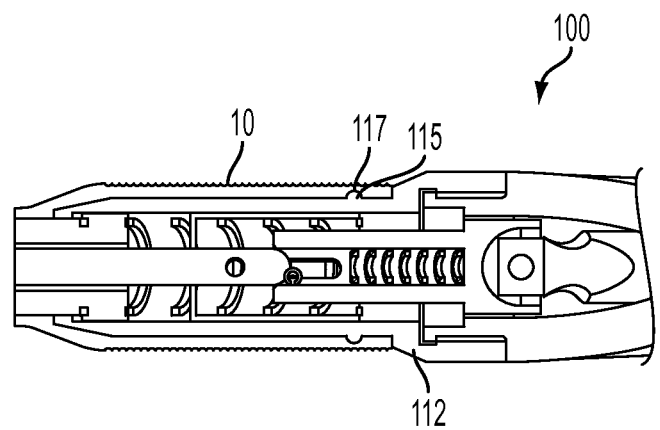
Figure 24A:
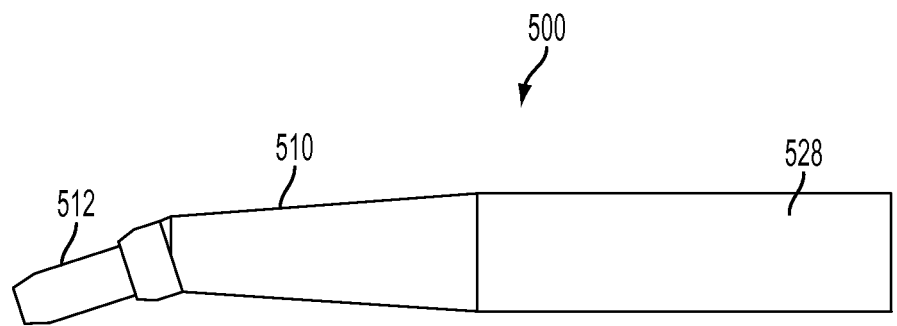
Figure 24B:
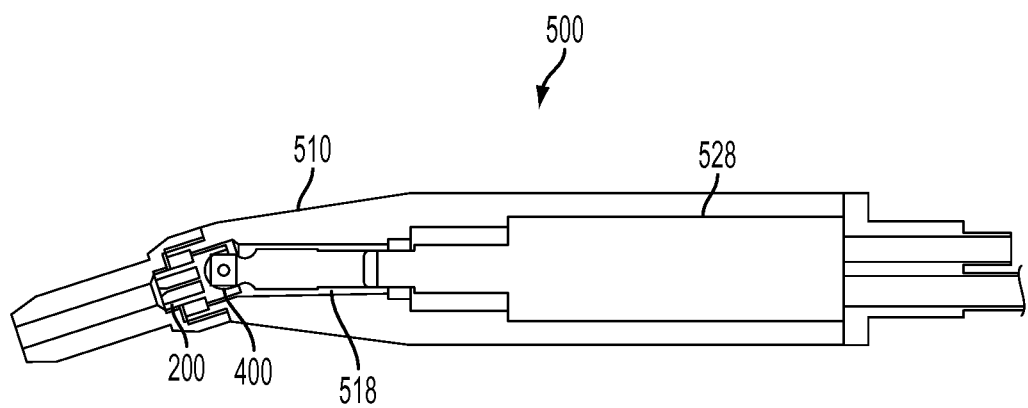
Figure 25:
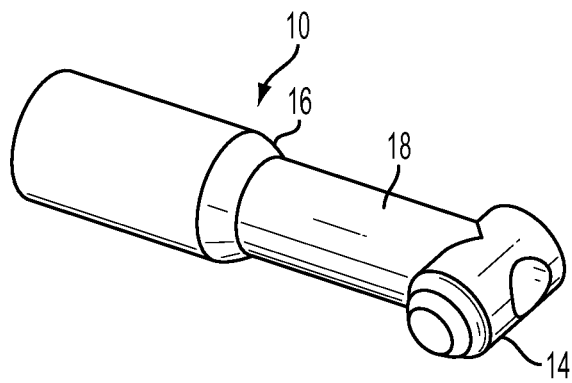
Figure 26:
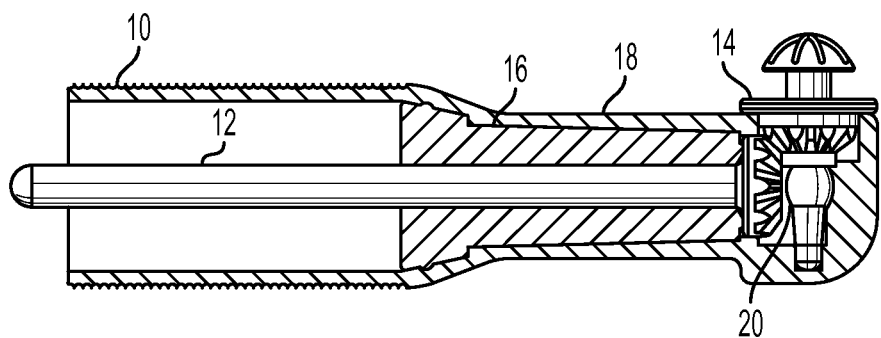

FIGS. 16A and 16B illustrate an adjustable angle adapter 500 with a micromotor 528 that is integral with the body 510 of the adjustable angle adapter 500. The adjustable angle adapter 500 can also have a nose 512 and a collet 200. Upon using an integral micromotor 528 with the adjustable angle adapter 500, the shaft 518 may be directly connected to both the micromotor 528 and multi-axis rotation joint 400. Using micromotors to drive dental equipment is well known by those in the art, and any micromotor 528 so capable is acceptable for use with the adjustable angle adapter 500. Examples of micromotors 528 include electrically-driven and pneumatically-driven motors. In the presently-illustrated adjustable angle adapter 500, the micromotor 528 is pneumatically driven.

What is claimed is:

1. An adjustable angle adapter for a prophy angle, comprising:
   a nose configured to receive a portion of the prophy angle;
   a rotating member positioned within the nose;
   a body adjustably connected to the nose;
   a shaft positioned within the body;
   a pivot connecting the body to the nose, the pivot comprising a groove configured for a ball bearing and opposing and mating faces which define a plane that is at an angle, other than perpendicular, to a rotational axis of the rotating member and a rotational axis of the shaft, wherein the ball bearing is passed through a channel formed within the pivot and the body, the channel parallel to the rotational axis of the shaft; and,
   a multi-axis rotation joint connecting the shaft to the rotating member, wherein
   the nose is rotatable relative to the body into a first configuration and a second configuration and the nose rotates relative to the body about a point on the plane, wherein the point is at the intersection of the plane and the rotational axis of the rotating member and at the intersection of the plane and the rotational axis of the shaft.

2. The adjustable angle adapter of claim 1, wherein
   in the first configuration, the shaft and the rotating member share a common rotational axis; and
   in the second configuration, the rotational axis of the shaft is at a non-zero degree angle to the rotational axis of the rotating member.

3. The adjustable angle adapter of claim 1, further comprising a lock, wherein
   in a unlocked configuration of the lock, the nose is rotatable relative to the body, and
   in a locked configuration of the lock, the lock preventing the nose from rotating relative to the body.

4. The adjustable angle adapter of claim 1, further comprising a motor integral with the body.

5. An adjustable angle adapter for a prophy angle, comprising:
   a nose configured to receive a portion of the prophy angle;
   a rotating member positioned within the nose;
   a body adjustably connected to the nose;
   a pivot connecting the body to the nose, the pivot comprising a groove configured for a ball bearing and opposing and mating faces which define a plane that is at an angle, other than perpendicular, to a rotational axis of the rotating member and a rotational axis of the shaft, wherein the ball bearing is passed through a channel formed within the pivot and the body, the channel parallel to the rotational axis of the shaft; and,
   a shaft positioned within the body and connected to the rotating member, wherein the nose is rotatable relative to the body into a first configuration and a second configuration while the shaft is rotating and the nose rotates relative to the body about a point on the plane, wherein the point is at the intersection of the plane and the rotational axis of the rotating member and at the intersection of the plane and the rotational axis of the shaft.

6. The adjustable angle adapter of claim 5, wherein
   in the first configuration, the shaft and the rotating member share a common rotational axis; and
   in the second configuration, the rotational axis of the shaft is at a non-zero degree angle to the rotational axis of the rotating member.

7. The adjustable angle adapter of claim 5, further comprising a lock, wherein
   in a unlocked configuration of the lock, the nose is rotatable relative to the body, and
   in a locked configuration of the lock, the lock preventing the nose from rotating relative to the body.

8. The adjustable angle adapter of claim 5, further comprising a motor integral with the body.

9. An adjustable angle adapter for a prophy angle, comprising:
   a nose configured to receive a portion of the prophy angle;
   a rotating member positioned within the nose;
   a body adjustably connected to the nose;
   a shaft positioned within the body;
   a pivot connecting the body to the nose, the pivot comprising a groove configured for a ball bearing; and,
   a coupler connecting the body and the pivot, the coupler comprising at least one ball bearing, wherein the at least one ball bearing is passed through a channel formed within the pivot and the body, the channel parallel to a rotational axis of the shaft.

10. The adjustable angle adapter of claim 9, wherein the nose is rotatable relative to the body into a first configuration and a second configuration, wherein
    in the first configuration, the shaft and the rotating member share a common rotational axis; and
    in the second configuration, a rotational axis of the shaft is at a non-zero degree angle to a rotational axis of the rotating member.

11. The adjustable angle adapter of claim 9, further comprising a lock, wherein
    in a unlocked configuration of the lock, the nose is rotatable relative to the body, and
    in a locked configuration of the lock, the lock preventing the nose from rotating relative to the body.

12. The adjustable angle adapter of claim 9, where the pivot further comprises opposing and mating faces that are at an angle, other than perpendicular, to a rotational axis of the rotating member and the rotational axis of the shaft.

13. The adjustable angle adapter of claim 9, further comprising a motor integral with the body.

14. An adjustable angle adapter for a prophy angle, comprising:
- a nose configured to receive a portion of the prophy angle;
- a rotating member positioned within the nose;
- a body adjustably connected to the nose, the nose is rotatable relative to the body into a first configuration and a second configuration;
- a shaft positioned within the body;
- a multi-axis rotation joint connecting the shaft to the rotating member;
- a pivot connecting the body to the nose, the pivot comprising a groove configured for a ball bearing and opposing and mating faces that are at an angle, other than perpendicular, to a rotational axis of the rotating member and a rotational axis to the shaft; and,
- a coupler connecting the body and the pivot, the coupler comprising at least one ball bearing, wherein the at least one ball bearing is passed through a channel formed within the pivot and the body, the channel parallel to the rotational axis of the shaft.

15. The adjustable angle adapter of claim 14, wherein the channel is covered by the nose.

16. An adjustable angle adapter for a prophy angle, comprising:
- a nose configured to receive a portion of the prophy angle;
- a rotating member positioned within the nose;
- a body adjustably connected to the nose, the nose is rotatable relative to the body into a first configuration and a second configuration;
- a shaft positioned within the body;
- a multi-axis rotation joint connecting the shaft to the rotating member;
- a pivot connecting the body to the nose, the pivot comprising a groove configured for a ball bearing and opposing and mating faces that are at an angle, other than perpendicular, to a rotational axis of the rotating member and a rotational axis to the shaft, wherein the ball bearing is passed through a channel formed within the pivot and the body, the channel parallel to the rotational axis of the shaft; and,
- a lock comprising a pin, the pivot configured to receive the pin.

17. An adjustable angle adapter for a prophy angle, comprising:
- a nose configured to receive a portion of the prophy angle;
- a rotating member positioned within the nose;
- a body adjustably connected to the nose, the nose is rotatable relative to the body into a first configuration and a second configuration;
- a shaft positioned within the body;
- a multi-axis rotation joint connecting the shaft to the rotating member;
- a pivot connecting the body to the nose, the pivot comprising a groove configured for a ball bearing and opposing and mating faces that are at an angle, other than perpendicular, to a rotational axis of the rotating member and a rotational axis to the shaft;
- a lock comprising a pin, the pivot configured to receive the pin; and,
- a coupler connecting the body and the pivot, the coupler comprising at least one ball bearing, wherein the at least one ball bearing is passed through a channel within the pivot and the body, the channel parallel to the rotational axis of the shaft.

18. An adjustable angle adapter for a prophy angle, comprising:
- a nose configured to receive a portion of the prophy angle;
- a rotating member positioned within the nose;
- a body adjustably connected to the nose, the nose is rotatable relative to the body into a first configuration and a second configuration;
- a shaft positioned within the body;
- a multi-axis rotation joint connecting the shaft to the rotating member;
- a lock comprising a pin, a pivot configured to receive the pin; and,
- a coupler connecting the body and the pivot, the coupler comprising at least one ball bearing, wherein the at least one ball bearing is passed through a channel formed within the pivot and the body, the channel parallel to a rotational axis of the shaft.

\* \* \* \* \*

UNITED STATES PATENT AND TRADEMARK OFFICE
CERTIFICATE OF CORRECTION

| | | Page 1 of 1 |
|---|---|---|
| PATENT NO. | : 8,668,494 B2 | |
| APPLICATION NO. | : 13/371026 | |
| DATED | : March 11, 2014 | |
| INVENTOR(S) | : Chris J. Carron and David G. Grither | |

It is certified that error appears in the above-identified patent and that said Letters Patent is hereby corrected as shown below:

In the Drawings:

- Figures 19A through 26 on drawing sheets 11 through 14 should be deleted

In the Specification:

- at column 2, line 50, remove the words "a second" and add the word "an" so to read "views of an adjustable angle adapter"

- at column 2, line 54, remove the words "a second" and add the word "an" so to read "views of an adjustable angle adapter"

- at column 4, line 21, replace the word "Staring" with the word "Starting" so to read "Starting with Figures"

- at column 6, lines 38 - 39, remove the words "of the inside diameter" so to read "is somewhat less than the inside diameter of the opening"

- at column 6, line 60, replace the words "or ration" in the phrase "range or ration" with the words "of rotation" so to read "range of rotation"

Signed and Sealed this
Fifth Day of August, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,668,494 B2 | Page 1 of 1 |
| APPLICATION NO. | : 13/371026 | |
| DATED | : March 11, 2014 | |
| INVENTOR(S) | : Chris J. Carron and David G. Grither | |

It is certified that error appears in the above-identified patent and that said Letters Patent is hereby corrected as shown below:

On the title page, under abstract "18 Claims, 14 Drawing Sheets" should read --18 Claims, 10 Drawing Sheets--

In the Drawings:

- Figures 19A through 26 on drawing sheets 11 through 14 should be deleted

In the Specification:

- at column 2, line 50, remove the words "a second" and add the word "an" so to read "views of an adjustable angle adapter"

- at column 2, line 54, remove the words "a second" and add the word "an" so to read "views of an adjustable angle adapter"

- at column 4, line 21, replace the word "Staring" with the word "Starting" so to read "Starting with Figures"

- at column 6, lines 38 - 39, remove the words "of the inside diameter" so to read "is somewhat less than the inside diameter of the opening"

- at column 6, line 60, replace the words "or ration" in the phrase "range or ration" with the words "of rotation" so to read "range of rotation"

This certificate supersedes the Certificate of Correction issued August 5, 2014.

Signed and Sealed this
Ninth Day of September, 2014

Michelle K. Lee
*Deputy Director of the United States Patent and Trademark Office*